United States Patent
Bell et al.

(10) Patent No.: US 8,420,859 B2
(45) Date of Patent: Apr. 16, 2013

(54) FORMULATIONS

(75) Inventors: Gordon Bell, Bracknell (GB); Ian David Tovey, Bracknell (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 12/293,894

(22) PCT Filed: Mar. 21, 2007

(86) PCT No.: PCT/GB2007/000986
§ 371 (c)(1),
(2), (4) Date: Sep. 22, 2008

(87) PCT Pub. No.: WO2007/107745
PCT Pub. Date: Sep. 27, 2007

(65) Prior Publication Data
US 2009/0227453 A1    Sep. 10, 2009

(30) Foreign Application Priority Data

Mar. 22, 2006  (GB) ................................. 0605780.6

(51) Int. Cl.
| C07C 235/06 | (2006.01) |
|---|---|
| C07C 235/14 | (2006.01) |
| A01N 25/32 | (2006.01) |

(52) U.S. Cl.
USPC ......................................... 564/201; 504/112

(58) Field of Classification Search ................. None
See application file for complete search history.

(56) References Cited

U.S. PATENT DOCUMENTS

| 2,990,331 A | 6/1961 | Horst et al. |
|---|---|---|
| 5,693,126 A | 12/1997 | Ito |

FOREIGN PATENT DOCUMENTS

| DE | 3618004 | 12/1987 |
|---|---|---|
| DE | 4112873 | 12/1997 |
| FR | 2564288 | 11/1985 |
| WO | 2006124899 | 11/2006 |

OTHER PUBLICATIONS

Database CAPLUS on STN, Acc. No. 1993:2468, Sehring, DE 4112873 (Oct. 22, 1992) (abstract).*
Nijburg, R.E.: and Gijsen R.M.R.: "Benefits and effectiveness of lactates as skin friendly ingredients in manual dishwashing;" SOFW-Journal, vol. 128, No. 5, 2002, pp. 104, XP002470080.
Budden, R. et al.: "Experiments on the toxic, sedative abd muscle relaxant effect of various drug solvents in mice," Pharm. Ther., vol. 5, 1979, pp. 467-474, XP002470081.
Shapiro et al: "Alpha-hydroxy amides and related compounds"; J. Am. Chem. Soc., vol. 81, Dec. 5, 1959, pp. 6322-6329, XP002470082, p. 6323-6326.
Ratchford, W. P. et al: "Preparation of N-substituted lactamides by aminolysis of methyl lactate"; J. Org. Chem., vol. 15, 1950, pp. 317-323, XP002470083.
Ratchford et al: "Preparation and properties of N-n-alkyllactamides;" 19500101; 19500000, vol. 15, Jan. 1, 1950, pp. 326-332, XP002479105.
Fein M. L. et al: "N-Substituted Lactamides;" Journal of the American Chemical Society, American Chemical Society, Washington, DC, US, vol. 75, May 5, 1953, pp. 2097-2099, XP002415482; ISSN: 0002-7863, p. 2098; table 1.

* cited by examiner

*Primary Examiner* — Brian J Davis
(74) *Attorney, Agent, or Firm* — Brian D. McAlhaney

(57) ABSTRACT

This invention relates to the use of lactamide compounds of formula (I): $CH_3CH(OH)C(=O)NR^1R^2$, where $R^1$ and $R^2$ are each independently hydrogen; or $C_{1-6}$ alkyl, $C_{2-6}$ alkenyl or $C_{3-6}$ cycloalkyl, each of which is optionally substituted by up to three substituents independently selected from phenyl, hydroxy, $C_{1-5}$ alkoxy, morpholinyl and $NR^3R^4$ where $R^3$ and $R^4$ are each independently $C^{1-3}$ alkyl; or phenyl optionally substituted by up to three substituents independently selected from $C_{1-3}$ alkyl; or $R^1$ and $R^2$ together with the nitrogen atom to which they are attached form a morpholinyl, pyrrolidinyl, piperidinyl or azepanyl ring, each of which is optionally substituted by up to three substituents independently selected from $C_{1-3}$ alkyl, in formulations to reduce the toxicity associated with other formulation components; to the use of certain lactamide compounds as solvents, especially in formulations, particularly in agrochemical formulations and in environmentally friendly formulations; to novel lactamide compounds; and to processes for preparing lactamide compounds.

7 Claims, No Drawings

FORMULATIONS

This application is a 371 of International Application No. PCT/GB2007/000986 filed Mar. 21, 2007, which claims priority to GB 0605780.6 filed Mar. 22, 2006, the contents of which are incorporated herein by reference.

This invention relates to the use of certain lactamide compounds in formulations to reduce the toxicity associated with other formulation components; to the use of certain lactamide compounds as solvents, especially in formulations, particularly in agrochemical formulations and in environmentally friendly formulations; to novel lactamide compounds; and to processes for preparing lactamide compounds.

Dimethyl lactamide is disclosed in DE 41 12 873 A1.

Certain lactamides are disclosed in Ratchford, W. P. and Fisher, C. H., Journal of Organic Chemistry, 1950, 15, 317-325; Ratchford, W. P., Journal of Organic Chemistry, 1950, 15, 326-332; Fein, M. L. and Filachione, E. M., Journal of the American Chemical Society, 1953, 75, 2097-2099; and U.S. Pat. No. 4,143,159.

Nowadays, the Formulation Chemist is required to address a number of environmental criteria when developing new formulations. Ideally, a suitable solvent will display many or all of the following properties: an excellent dissolving power for pesticides or other organic molecules; made from plant or animal renewable resources; low skin irritation; an ability to reduce the skin irritation associated with aggressive formulation components, such as sodium lauryl sulphate; low ecotoxicity, for example to daphnia; low volatile organic content; and a high flash point. The compounds of the present invention each display all or many of these properties; in particular, they may reduce the toxicity [which may be toxicity to animals, especially mammals, or to plants] associated with other components with which they may be present Suitably, dermal toxicity, oral toxicity or eye toxicity may be reduced. A compound of the present invention may be present with another component in a formulation either by virtue of combining the two in a formulation prepared in advance of use [such a formulation is then used in concentrated form or may be used in diluted form, for example dilution with water] or by combining the two at the point of use [that is, in situ preparation of the formulation].

Accordingly, the present invention provides the use of a compound of formula (I) in a formulation to reduce the toxicity associated with at least one other component present in the formulation

$$CH_3CH(OH)C(=O)NR^1R^2 \quad (I)$$

where $R^1$ and $R^2$ are each independently hydrogen; or $C_{1-6}$ alkyl, $C_{2-6}$ alkenyl or $C_{3-6}$ cycloalkyl, each of which is optionally substituted by up to three substituents independently selected from phenyl, hydroxy, $C_{1-5}$ alkoxy, morpholinyl and $NR^3R^4$ where $R^3$ and $R^4$ are each independently $C_{1-3}$ alkyl; or phenyl optionally substituted by up to three substituents independently selected from $C_{1-3}$ alkyl; or $R^1$ and $R^2$ together with the nitrogen atom to which they are attached form a morpholinyl, pyrrolidinyl, piperidinyl or azepanyl ring, each of which is optionally substituted by up to three substituents independently selected from $C_{1-3}$ alkyl.

In one suitable aspect, $R^1$ and $R^2$ are each independently hydrogen; or $C_{1-6}$ alkyl, $C_{2-6}$ alkenyl or $C_{3-6}$ cycloalkyl, each of which is optionally substituted by up to three substituents independently selected from phenyl, hydroxy, $C_{1-5}$ alkoxy, morpholinyl and $NR^3R^4$ where $R^3$ and $R^4$ are each independently $C_{1-3}$ alkyl; or $R^1$ and $R^2$ together with the nitrogen atom to which they are attached form a morpholinyl ring which is optionally substituted by up to three substituents independently selected from $C_{1-3}$ alkyl.

In a more suitable aspect $R^1$ and $R^2$ are each independently hydrogen; or $C_{1-6}$ alkyl which is optionally substituted by up to three substituents independently selected from phenyl, hydroxy, $C_{1-5}$ alkoxy, morpholinyl and $NR^3R^4$ where $R^3$ and $R^4$ are each independently $C_{1-3}$ alkyl; or $R^1$ and $R^2$ together with the nitrogen atom to which they are attached form a morpholinyl ring which is optionally substituted by up to three substituents independently selected from $C_{1-3}$ alkyl.

In an even more suitable aspect, $R^1$ and $R^2$ are each independently hydrogen; or $C_{1-6}$ alkyl; or $R^1$ and $R^2$ together with the nitrogen atom to which they are attached form a morpholinyl ring.

In an even further suitable aspect, $R^1$ is methyl and $R^2$ is methyl, ethyl, propyl or butyl [yet more suitably $R^2$ is methyl, propyl or butyl]; or $R^1$ and $R^2$ together with the nitrogen atom to which they are attached form a morpholinyl ring.

Suitably $R^3$ is methyl.

Suitably $R^4$ is methyl.

For each optional substituent, it is preferred that it is a methyl group.

Suitably alkyl groups are branched; most suitably with methyl groups.

Suitably the invention provides the use of a compound of formula (I) in a formulation to reduce the toxicity associated with at least one other component present in the formulation where $R^1$ and $R^2$ are each independently hydrogen, $C_{1-6}$ alkyl, $C_{2-6}$ alkenyl or $C_{3-6}$ cycloalkyl; or $R^1$ and $R^2$ together with the nitrogen atom to which they are attached form a pyrrolidinyl, piperidinyl or azepanyl ring.

Suitably, the compound of formula (I) is used in a formulation to reduce the toxicity associated with a surfactant [i.e. the "at least one other component present in the formulation" is a surfactant], which may be non-ionic [for example a nonylphenol ethoxylate or an alcohol ethoxylate], anionic [for example an alkyl sulphate, such as sodium lauryl sulphate, or a sulphonate, such as calcium dodecylbenzene sulphonate] or cationic [for example a tertiary amine, such as a tertiary amine ethoxylate; or a tri-alkyl ammonium salt, such as cetyl trimethyl ammonium bromide]. More suitably, the compound of formula (I) is used in a formulation to reduce the toxicity associated with sodium lauryl sulphate [i.e. the "at least one other component present in the formulation" is sodium lauryl sulphate].

These compounds may be used effectively as solvents. Therefore in another aspect, the present invention provides the use of a compound of formula (I) as defined above; provided that $R^1$ is not methyl when $R^2$ is methyl. Suitably, to act as a solvent, a compound of formula (I) is liquid at room temperature and pressure.

Many of the compounds disclosed by the present invention are novel.

Therefore in a further aspect, the present invention provides a compound of formula (I) where $R^1$ and $R^2$ are each independently hydrogen; or $C_{1-6}$ alkyl, $C_{2-6}$ alkenyl or $C_{3-6}$ cycloalkyl, each of which is optionally substituted by up to three substituents independently selected from phenyl, hydroxy, $C_{1-5}$ alkoxy, morpholinyl and $NR^3R^4$ where $R^3$ and $R^4$ are each independently $C_{1-3}$ alkyl; or phenyl optionally substituted by up to three substituents independently selected from $C_{1-3}$ alkyl; or $R^1$ and $R^2$ together with the nitrogen atom to which they are attached form a morpholinyl, pyrrolidinyl, piperidinyl or azepanyl ring, each of which is optionally substituted by up to three substituents independently selected from $C_{1-3}$ alkyl; provided that $R^1$ is not hydrogen, methyl, ethyl, propyl, n-butyl, sec-butyl, iso-butyl, n-amyl, iso-amyl, iso-butylenyl, n-hexyl, 1-3-dimethylbutyl, allyl, $CH_2CH_2OH$, 2-hydroxypropyl, 2-hydroxyisobutyl, 1,3-dihydroxy-2-methyl-2-propyl, tris-hydroxymethyl-methyl, $CH_2CH_2OCH_3$, cyclohexyl, phenyl, benzyl, α-methylbenzyl, β-phenylethyl, 3-hydroxypropyl or 1-hydroxy-2-butyl when $R^2$ is hydrogen;
$R^1$ is not methyl, allyl or phenyl when $R^2$ is methyl;
$R^1$ is not ethyl when $R^2$ is ethyl;
$R^1$ is not n-butyl when $R^2$ is n-butyl;
$R^1$ is not iso-butyl when $R^2$ is iso-butyl;
$R^1$ is not n-amyl when $R^2$ is n-amyl;
$R^1$ is not iso-amyl when $R^2$ is iso-amyl;
$R^1$ is not n-hexyl when $R^2$ is n-hexyl;
$R^1$ is not allyl when $R^2$ is allyl;
$R^1$ is not butyl or phenyl when $R^2$ is phenyl;
$R^1$ is not benzyl when $R^2$ is benzyl;
$R^1$ is not $CH_2CH_2OH$ or ethyl when $R^2$ is $CH_2CH_2OH$;
$R^1$ is not 2-hydroxypropyl when $R^2$ is 2-hydroxypropyl; and
$R^1$ and $R^2$ together with the nitrogen atom to which they are attached do not form a morpholinyl, pyrrolidinyl or piperidinyl unsubstituted ring.

Suitably, the present invention provides a compound of formula (I) where $R^1$ and $R^2$ are each independently hydrogen, $C_{1-6}$ alkyl, $C_{2-6}$ alkenyl or $C_{3-6}$ cycloalkyl; or $R^1$ and $R^2$ together with the nitrogen atom to which they are attached form a pyrrolidinyl, piperidinyl or azepanyl ring; provided that $R^1$ is not hydrogen, methyl, ethyl, n-propyl, iso-propyl, n-butyl, sec-butyl, iso-butyl, n-amyl, iso-amyl or iso-butylenyl when $R^2$ is hydrogen; $R^1$ is not methyl when $R^2$ is methyl; $R^1$ is not ethyl when $R^2$ is ethyl; and $R^1$ is not n-butyl when $R^2$ is n-butyl; suitably $R^1$ and $R^2$ are each independently hydrogen or $C_{1-6}$ alkyl, $C_{2-6}$ alkenyl or $C_{3-6}$ cycloalkyl; and more suitably $R^1$ is hydrogen.

Alkyl groups and moieties are straight or branched chains. Examples are methyl, ethyl, iso-propyl, n-propyl, n-butyl, sec-butyl, tert-butyl, n-amyl and iso-amyl[3-methylbutyl].

Alkenyl groups and moieties may be in the form of straight or branched chains and, where appropriate, may be of either the (E)- or (Z)-configuration. Examples are vinyl and allyl.

Cycloalkyl includes cyclopropyl, cyclopentyl and cyclohexyl.

Suitably $R^1$ and $R^2$ are each independently hydrogen or $C_{1-6}$ alkyl, $C_{2-6}$ alkenyl or $C_{3-6}$ cycloalkyl; more suitably hydrogen or $C_{1-6}$ alkyl; yet more suitably hydrogen or $C_{1-5}$ alkyl; and still more suitably hydrogen or $C_{1-4}$ alkyl. In one aspect, even more suitably, $R^1$ is hydrogen. In another aspect, even more suitably, $R^1$ is methyl.

The compounds of the invention may be used in a variety of end use applications (including agrochemical formulations), particularly as solvents. These solvents may be used with a wide variety of materials, including herbicides, fungicides, acaricides, nematicides and insecticides [and also plant growth regulators].

The compounds of the invention may be used to formulate solutions of a variety of materials, including agrochemicals, which may be formulated as emulsion or dispersion concentrates, emulsions in water or oil, microencapsulated formulations, aerosol sprays or fogging formulations; and these may be further formulated into granular materials or powders, for example for dry application or as water-dispersible formulations. The solutions so formed may also be used directly on soil or plants or in other non-agrochemical applications. The low toxicity of the solutions makes them particularly suitable for skin creams, lotions, sun creams, personal hygiene products and pharmaceutical formulations, such as tablets, suppositories, inhalers, dermal creams and potions.

The low toxicity and excellent environmental profile of these compounds mean that they are particularly useful in applications where the minimisation of pollution is desired. Examples of such applications include paper making, water treatment, forestry applications, public health treatments, use in municipal pools and other water courses, in applications near rivers, lakes, reservoirs or seas and in applications where release to the atmosphere has to be minimised or controlled and where damage to the atmosphere is not desirable. Examples include use in exterior and interior paints, coatings, varnishes, waxes or other protectant layers or opacifiers, colourants or screens; in dyeing, pigmentation or the use of inks; in cleaning products designed for the home, garden or industrial applications; and in soap or detergent applications for industrial, home or environmental usage. The compounds of the present invention may also be used in shampoos, household detergency and in household cleaners [for example oven cleaners and surface cleaners].

The compounds of the present invention are particularly valuable in formulations where contact with either human or animal skin or eyes is required or may occur by accident. Applications such as the use of shampoo or bodily cleaning fluids [such as shower gels, hand or body wipes and medical wipes] may benefit from the safe nature of these solvents, which may form part of a cleaning formulation and which may also reduce the irritancy of some of the other ingredients, such as surfactants. In a similar fashion the application of pharmaceutical or veterinary products directly to the skin or eyes may benefit by a reduction in the overall irritation caused by a formulation when it relies on a compound of the present invention. The compounds of the present invention may also be used for anti-bacterial purposes. Hand cleansers and fluids used to clean floors, kitchens or vehicles may also benefit from the inherent reduction in risk associated with the safening nature of the solvent. Industrial processes such as electroplating and coating often require strong solvents and/or acids in order to clean and degrease metal or similar surfaces. The compounds of the present invention may reduce the overall corrosivity of such fluids which would reduce the risk associated with the manufacturing process.

The low toxicities and excellent dermal properties of these compounds also mean that they are suitable for a wide array of pharmaceutical, veterinary and personal hygiene applications. They are particularly valuable for skin application, oral dosing, injection, suppository and subcutaneous or intra-lipid insertion, for example in polymer-controlled release devices.

The compounds of the present invention have exceptional dissolving power for a wide variety of agrochemicals, pharmaceuticals and other commercially valuable compounds, plus the dissolving power also extends to dissolution of dirt, grease or waxes; have very low toxicity to mammals, birds, fish and other aquatic organisms; have low dermal toxicity or irritancy and, in addition, the solvents reduce the dermal toxicity of highly damaging compounds such as sodium lauryl sulphate and other surfactants; have high flash points which mean that they have a benefit in terms of the safety requirements needed for storage, transport and use; have low vapour pressures which mean that they have low levels of volatile organic compound emissions; are manufactured from natural materials which are readily renewable from plant or animal sources; and are inexpensive to manufacture because they are produced from readily available and inexpensive raw ingredients.

The compounds of the present invention may be prepared by reacting a compound of formula (III) [CH$_3$CH(OH)C(=O)OR$^5$ (III)] where OR$^5$ is a leaving group, with a compound of formula (II) [HNR$^1$R$^2$ (II)] where R$^1$ and R$^2$ are as defined above.

Accordingly, the present invention further provides a process for making a compound of formula (I) as defined above comprising the step of reacting a compound of formula (III) [CH$_3$CH(OH)C(=O)OR$^5$ (III)] where OR$^5$ is a leaving group with a compound of formula (II) [HNR$^1$R$^2$ (II)] where R$^1$ and R$^2$ are as above.

Suitably R$^5$ is C$_{1-4}$ alkyl.

This process produces HOR$^5$ as a by-product; a cleaner reaction avoids this by-product: the compounds of the present invention may also be prepared by reacting lactide [3,6-dimethyl-[1,4]-dioxane-2,5-dione] with a compound of formula (II) [HNR$^1$R$^2$ (II)] where R$^1$ and R$^2$ are as defined above. Schematically, such a reaction is shown below:

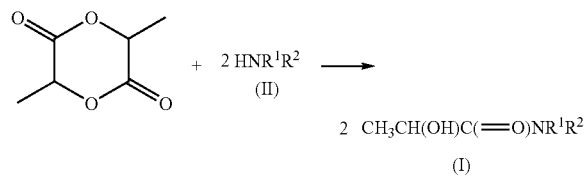

The present invention is not limited to the above reaction scheme; it illustrates how lactide [3,6-dimethyl-[1,4]-dioxane-2,5-dione] may be converted to a lactamide by reacting lactide with an amine [suitably a primary or secondary amine].

Therefore the present invention also provides a process for making a lactamide compound comprising the step of reacting lactide [3,6-dimethyl-[1,4]-dioxane-2,5-dione] with an amine. Furthermore it provides a process for making a compound of formula (I) as defined above comprising the step of reacting lactide with a compound of formula (II) [HNR$^1$R$^2$ (II)] where R$^1$ and R$^2$ are as defined above.

Suitably either process of the present invention may be operated solvent-free.

The invention is illustrated by the following Examples in which:

g=grammes ° C.=degrees centigrade

Unless otherwise stated, each concentration is expressed as percentage by weight.

EXAMPLE 1

Skin irritation and damage can be measured most easily by a well-known SIFT (Skin Integrity Function Test) procedure measuring the electrical resistance of the skin after exposure to the material of interest and comparing this to the electrical resistance of untreated skin. In this particular Example, solutions of 1% and 10% w/w dimethyl lactamide were prepared and tested in comparison with a 10% w/w solution of sodium lauryl sulphate (SLS). SLS is used in shampoo and toothpaste formulations and is a suitable control because much is known about its irritating behaviour on human skin and eye tissue. Table 1 shows the mean result from five measurements with each sample as well as the calculated standard error on each mean. The results for the two concentrations of dimethyl lactamide are within the experimental error range of the untreated control thus displaying the remarkably benign behaviour of this solvent on skin. By contrast the damage caused by the 10% SLS solution was significantly higher than that caused by either of the lactamide solutions.

TABLE 1

Electrical resistivity measurements post-treatment of skin subjected to each solution.

| Sample | Electrical resistivity/ kilo ohms | Std. error |
| --- | --- | --- |
| Untreated control | 8.00 | 1.39 |
| 10% dimethyl lactamide solution | 7.72 | 2.05 |
| 1% dimethyl lactamide solution | 8.04 | 0.72 |
| 10% SLS solution | 0.91 | 0.05 |

EXAMPLE 2

Dimethyl lactamide was shown to reduce the damage caused by skin irritants. A SIFT (as discussed in Example 1) was carried out to compare the damage caused by a 0.5% w/w SLS aqueous solution compared to an aqueous sample containing 0.5% SLS plus 10% w/w dimethyl lactamide. The results in Table 2 show that skin treated with dimethyl lactamide plus SLS together suffered significantly less damage that skin exposed to SLS alone. For comparison the damages caused by 1% and 10% SLS solutions and also the value for an untreated control have been included.

TABLE 2

Electrical resistivity measurements on skin exposed to SLS and to dimethyl lactamide.

| Sample | Electrical resistivity/ kilo ohms | Std. error |
| --- | --- | --- |
| Untreated control | 8.00 | 1.39 |
| 0.5% SLS with 10% dimethyl lactamide solution | 3.17 | 0.65 |
| 0.5% SLS solution | 2.03 | 0.33 |
| 1.0% SLS solution | 1.84 | 0.57 |
| 10.0% SLS solution | 0.91 | 0.05 |

EXAMPLE 3

The toxicity of solvents to daphnia is a suitable way to assess the likely ecological impact of a spillage and to the potential environmental impact of the material in use. In this test various concentrations of dimethyl lactamide were used in order to find the point at which *daphnia magna* suffered reduced mobility. *Daphnia magna* in tanks were exposed for 48 hours to solutions of dimethyl lactamide. The concentration of dimethyl lactamide in water at which 50% reduced mobility [EC50] was detected is between 0.1% and 1% w/w.

EXAMPLE 4

The flammability of solvents is of concern to minimise risk during storage, transport and use. Typically the risk is assessed by measuring the flash point of the solvent. The flash point of dimethyl lactamide was measured using a Seta flash 3 closed cup tester model 30000-0. The measured value was 108° C.

EXAMPLE 5

A major environmental concern associated with solvents is the likelihood of volatile organic compound (voc) being released and transferred to the upper atmosphere. A measure of this tendency is the vapour pressure of the solvent as this determines the driving force to enter the vapour phase. The measured vapour pressure of dimethyl lactamide was found to be between 0.08 and 0.2 mmHg at 20° C.

EXAMPLE 6

Formulations that are applied to crop plants can often lead to phytotoxic damage. This damage may take the form of the formation of necrotic spots where sprayed formulation has landed on leaf surfaces or it may take the form of chlorosis or larger scale damage to the plant such as dessication and death. In order to assess the safety of solvents to plant species they were sprayed at high usage rates and high water volumes onto very sensitive, young plants.

The plant species *amaranthus retroflexus* (AMARE), *alopecurus myosuorides* (ALOMY), *chenopodium album* (CHEAL) and *digitaria sanguinalis* (DIGSA) were grown from seed under glass house conditions until they reached the first leaf stage. A solvent was dissolved in distilled water at a rate of 1% w/w and sprayed onto the plants at a rate of 2500 litres per hectare using a laboratory track sprayer. The plants were maintained in the glasshouse for a period of 2 weeks in order to observe any effects on the plants. Untreated plants were grown and kept under the same conditions as a direct comparison to the treated samples. A second set of identical plants was also sprayed with the novel solvent however in this case 0.5% of the commercial surfactant Tween 20 (T) was also added to the spray solution. In this experiment control plants for comparison were also sprayed with 0.5% Tween 20 but not with the solvent. Plants were examined after 1, 2, 6, 7, 9 and 13 days to try to find evidence of damage to the treated plants. All experiments were carried out in duplicate. The following solvents were tested using this procedure; the observed damages to the plants are listed in Table 3.

TABLE 3

| Solvent | Observed damage with solvent | Observed damage with solvent and Tween 20 |
| --- | --- | --- |
| N-propyl morpholynyl lactamide | None | None |
| N-2-hydroxyethyl lactamide | None | None |
| 3-diethylamino propyl lactamide | None | Slight damage to AMARE, CHEAL, not replicated |
| N-1,3-dimethyl butyl lactamide | None | None |
| N-benzyl Lactamide | None | None |
| N-sec-butyl lactamide | None | None |
| N-2-hydroxyethyl piperidinyl lactamide | None | None |
| N-allyl lactamide | None | None |
| N-3-butoxypropyl lactamide | None | None |
| N-isobutyl lactamide | None | None |
| N-isopropyl Lactamide | None | None |
| N-1-ethyl-2-hydroxyethyl lactamide | Damage to one AMARE, not replicated | None |
| N-ethyl-N-2-hydroxyethyl lactamide | None | None |
| N-1-hyroxyethylbutyl lactamide | None | None |
| N-pyrrolidinyl lactamide | None | None |
| N-morpholinyl lactamide | None | None |
| N-hydroxyethyl-N-benzyl lactamide | None | None |
| N-ethyl lactamide | None | None |
| N-methyl-N-butyl lactamide | None | None |
| N-methyl-N-propyl lactamide | None | None |

EXAMPLE 7

A sample of a solvent (200 microlitres) was added to a 4 ml volume glass vial. The pesticide cyproconazole was added to the vial and shaken to allow thorough mixing. The vial was left to equilibrate at 25° C. for 24 hours after which time it was examined visually. If the solid had dissolved a further quantity of cyproconazole was added, the vial shaken and then left for another 24 hours. This process was repeated until a saturated solution had formed after which time the vial was left to equilibrate for one week. The glass vial was thoroughly shaken using a laboratory Whirlimixer™ (T) (Fisons Scientific Instruments Limited), once per day, during this period. After this time the sample was centrifuged, the supernatant was sampled and analysed by HPLC with reference to a known weight of pure cyproconazole, in order to determine the concentration of cyproconazole in solution.

Table 4 demonstrates that lactamide solvents have excellent solubilising power for the pesticide.

TABLE 4

| Solvent | % cyproconazole in solution |
| --- | --- |
| N-butoxypropyl lactamide | 17.3% w/w |
| 1-(hydroxyethyl) piperidinyl lactamide | 19.3% w/w |
| N-methyl-N-propyl lactamide | 27.3% w/w |
| N-(1-ethylpropyl) lactamide | 12.0% w/w |
| N,N-dimethyl lactamide | 36.3% w/w |
| N-1,4-dimethylpentyl lactamide | 10.5% w/w |
| N-(2-hydroxyethyl)-N-benzyl lactamide | 25.0% w/w |
| N-Morpholinyl lactamide | 28.3% w/w |
| N-methyl-N-butyl lactamide | 33.0% w/w |
| N-Isobutyl lactamide | 16.6% w/w |
| N-Allyl lactamide | 18.1% w/w |
| N-Ethyl lactamide | 18.8% w/w |
| N-Ethyl-N-(2-hydroxyethyl) lactamide | 18.2% w/w |
| N-isopropyl lactamide | 20.5% w/w |

EXAMPLE 8

This example illustrates the preparation of certain compounds of the present invention.

The amines used were commercial samples supplied by Fisher Scientific or Sigma Aldrich. Amines were reacted with one of the following:

(−)-Ethyl(S)-2-hydroxypropionate ("Ethyl-5-lactate", Ex Sigma Aldrich, 98%)

(−)-Ethyl(S)-2-hydroxypropionate ("Ethyl-L-lactate", Ex Fluka, >99%)

3,6-dimethyl-1,4-dioxane-2,5-dione ("Lactide", Ex Aldrich, 99%)

Initially reactions were performed in a microwave reactor under the conditions listed in Table 5. Due to the restricted volumes possible and in light of the rapid reactions seen, further reactions were carried out under ambient conditions and over an increased timescale. Reactions were monitored using FT-IR spectroscopy via the reduction in the ester band from ethyl-lactate at ~1750 cm$^{-1}$ and the corresponding increase in the amide bands at ~1630 cm$^{-1}$ and ~1550 cm$^{-1}$. Selected samples were purified via preparatory HPLC and the compounds were identified via GC-MS and NMR.

A cleaner, novel synthetic route was later utilised where the amines were reacted with lactide (3,6-dimethyl-1,4-dioxane-2,5-dione).

TABLE 5

| Amine | Moles | Reacted With | Moles | Reaction Conditions | Yield |
|---|---|---|---|---|---|
| Ethylamine | 0.126 | Ethyl-S-lactate | 0.126 | Microwave Reactor, 200° C., 20 Bar, 3 minutes | >75% |
| Ethanolamine | 0.164 | Ethyl-S-lactate | 0.164 | Microwave Reactor, 200° C., 15 Bar, 30 minutes | >95% |
| Isopropylamine | 0.116 | Ethyl-S-lactate | 0.116 | Microwave Reactor, 200° C., 18 Bar, 30 minutes | >75% |
| Diethanolamine | 0.104 | Ethyl-S-lactate | 0.104 | Microwave Reactor, 200° C., 15 Bar, 30 minutes | >75% |
| Morpholine | 0.114 | Ethyl-S-lactate | 0.114 | Microwave Reactor, 200° C., 9 Bar, 30 minutes | >75% |
| Benzylamine | 0.091 | Ethyl-S-lactate | 0.091 | Microwave Reactor, 200° C., 13 Bar, 30 minutes | >75% |
| Diethylamine | 0.096 | Ethyl-S-lactate | 0.096 | Microwave Reactor, 200° C., 15 Bar, 30 minutes | >50% |
| N-methyl-tert-butylamine | 0.037 | Ethyl-S-lactate | 0.037 | Microwave Reactor, 200° C., 12 Bar, 30 minutes | >25% |
| N-ethylisopropylamine | 0.037 | Ethyl-S-lactate | 0.037 | Microwave Reactor, 175° C., 8 Bar, 30 minutes | >25% |
| sec-Butylamine | 0.098 | Ethyl-S-lactate | 0.098 | Microwave Reactor, 200° C., 14 Bar, 30 minutes | >75% |
| 1-ethylpropylamine | 0.085 | Ethyl-S-lactate | 0.085 | Microwave Reactor, 200° C., 12 Bar, 30 minutes | >75% |
| N-isopropylmethylamine | 0.096 | Ethyl-S-lactate | 0.096 | Microwave Reactor, 150° C., 3 Bar, 30 minutes | >25% |
| tert-Butylamine | 0.095 | Ethyl-S-lactate | 0.095 | Microwave Reactor, 200° C., 17 Bar, 30 minutes | >95% |
| Pyrrolidine | 0.119 | Ethyl-S-lactate | 0.119 | Microwave Reactor, 200° C., 14 Bar, 30 minutes | >75% |
| 1,3-dimethylbutylamine | 0.030 | Ethyl-S-lactate | 0.030 | Microwave Reactor, 200° C., 10 Bar, 30 minutes | >50% |
| 2-(ethylamino)ethanol | 0.204 | Ethyl-L-lactate | 0.183 | 4 days at Ambient Temperature & Pressure | >75% |
| 2-amino-1-butanol | 0.208 | Ethyl-L-lactate | 0.188 | 4 days at Ambient Temperature & Pressure | >75% |
| allylamine | 0.267 | Ethyl-L-lactate | 0.240 | 4 days at Ambient Temperature & Pressure | >75% |
| Isobutylamine | 0.199 | Ethyl-L-lactate | 0.179 | 4 days at Ambient Temperature & Pressure | >75% |
| 1-ethylpropylamine | 0.171 | Ethyl-L-lactate | 0.154 | 4 days at Ambient Temperature & Pressure | >25% |
| tert-amylamine | 0.170 | Ethyl-L-lactate | 0.153 | 3 days at Ambient Temperature & Pressure | <25% |
| Dipropylamine | 0.146 | Ethyl-L-lactate | 0.131 | 2 days at Ambient Temperature & Pressure | Negligible |
| Hexylamine | 0.151 | Ethyl-L-lactate | 0.136 | 3 days at Ambient Temperature & Pressure | >75% |
| DL-2-amino-1-pentanol | 0.044 | Ethyl-L-lactate | 0.039 | 3 days at Ambient Temperature & Pressure | >75% |
| N-hexylmethylamine | 0.130 | Ethyl-L-lactate | 0.117 | 2 days at Ambient Temperature & Pressure | >50% |
| N-methylpropylamine | 0.047 | Ethyl-L-lactate | 0.042 | 4 days at Ambient Temperature & Pressure | >50% |
| Dipropylamine | 0.047 | Lactide | 0.025 | 2 hours at 50° C. | <10% |
| Benzylamine | 0.053 | Lactide | 0.028 | 1 hour at 40° C. | >95% |
| 2-benzylaminoethanol | 0.069 | Lactide | 0.035 | 5 hours at 55° C. | >25% |
| N-methylbenzylamine | 0.074 | Lactide | 0.038 | 12 days at Ambient Temperature & Pressure | >50% |
| N-methylbutylamine | 0.078 | Lactide | 0.040 | 12 days at Ambient Temperature & Pressure | >50% |
| 3-diethylamino-propylamine | 0.065 | Lactide | 0.033 | 12 days at Ambient Temperature & Pressure | >75% |
| 2-Ethyl-1-Hexylamine | 0.166 | Lactide | 0.108 | 4 days at Ambient Temperature & Pressure | >95% |
| 3-N-Butoxy Propylamine | 0.056 | Lactide | 0.034 | 4 days at Ambient Temperature & Pressure | >25% |

TABLE 5-continued

| Amine | Moles | Reacted With | Moles | Reaction Conditions | Yield |
|---|---|---|---|---|---|
| 3-Pentylamine | 0.059 | Lactide | 0.040 | 4 days at Ambient Temperature & Pressure | >95% |
| N-(3-Aminopropyl)Morpholine | 0.067 | Lactide | 0.035 | 4 days at Ambient Temperature & Pressure | >95% |
| N-Methylaniline | 0.081 | Lactide | 0.042 | 4 days at Ambient Temperature & Pressure | >25% |

EXAMPLE 9

Daphnia screening is commonly carried out to assess the inherent toxicity of chemicals. In this test five daphnia were placed in a beaker full of water held between 18 and 19° C. A lactamide chemical of interest was introduced to a concentration of 100 mg/l and the daphnia were monitored over 24 and 48 hours. Any daphnia which became immobile were recorded and the number was used for the assessment. If less than half of the daphnia were immobile after 48 hours the $EC_{50}$ (48 hours) figure was classified as being >100 mg/l [otherwise, it would be less than or equal to 100 mg/l]. The lactamides of Table 6 were tested and their $EC_{50}$ figures are tabulated (each experiment was replicated four times and in fact in all these tests none of the daphnia died):

TABLE 6

| Test substance | $EC_{50}$ (48 hours) [mg/l] |
|---|---|
| N-(2-ethylhexyl) lactamide | >100 |
| N-methyl-N-n-butyl lactamide | >100 |
| N-3-butoxypropyl lactamide | >100 |
| N-morpholinyl lactamide | >100 |
| N-allyl lactamide | >100 |
| N-[1-(hydroxyethyl)]-N-piperidinyl lactamide | >100 |
| N-ethyl-N-(2-hydroxyethyl) lactamide | >100 |
| N-(2-hydroxyethyl)-N-benzyl lactamide | >100 |
| N-methyl-N-n-propyl lactamide | >100 |
| N-(1-ethylpropyl) lactamide | >100 |

The invention claimed is:
1. A method of reducing the mammalian toxicity associated with at least one other component in a formulation comprising adding a compound of formula (I) to the formulation in an amount sufficient to reduce the mammalian toxicity associated with the at least one other component present in the formulation

$$CH_3CH(OH)C(=O)NR^1R^2 \qquad (I)$$

where $R^1$ and $R^2$ are each independently hydrogen; $C_{1-6}$, $C_{2-6}$ alkenyl or $C_{3-6}$ cycloalkyl.

2. The method of claim 1 wherein a compound of formula (I) is used as a solvent.

3. The method of claim 1 where $R^1$ is methyl and $R^2$ is $C_{1-6}$, $C_{2-6}$ alkenyl or $C_{3-6}$ cycloalkyl.

4. The method of claim 1 where $R^1$ is methyl and $R^2$ is $C_{1-4}$ alkyl.

5. The method of claim 1 where $R^1$ is hydrogen.

6. The method of claim 1 where the at least one other component is a surfactant.

7. The method of claim 1 where the at least one other component is sodium lauryl sulphate.

* * * * *

UNITED STATES PATENT AND TRADEMARK OFFICE
CERTIFICATE OF CORRECTION

PATENT NO. : 8,420,859 B2  
APPLICATION NO. : 12/293894  
DATED : April 16, 2013  
INVENTOR(S) : Bell et al.

Page 1 of 1

It is certified that error appears in the above-identified patent and that said Letters Patent is hereby corrected as shown below:

In the Claims

At column 12, in claim 1, insert --alkly-- after --C1-6--

Signed and Sealed this  
Thirteenth Day of August, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,420,859 B2  
APPLICATION NO. : 12/293894  
DATED : April 16, 2013  
INVENTOR(S) : Bell et al.

Page 1 of 1

It is certified that error appears in the above-identified patent and that said Letters Patent is hereby corrected as shown below:

In the Claims

Column 12, line 30 (Claim 1, line 8) insert --alkly-- after "C1-6"

This certificate supersedes the Certificate of Correction issued August 13, 2013.

Signed and Sealed this
Third Day of September, 2013

Teresa Stanek Rea
*Acting Director of the United States Patent and Trademark Office*